United States Patent [19]

Yabe

[11] Patent Number: 4,509,507
[45] Date of Patent: Apr. 9, 1985

[54] ENDOSCOPE APPARATUS

[75] Inventor: Hisao Yabe, Tokyo, Japan

[73] Assignee: Olympus Optical Co., Ltd., Tokyo, Japan

[21] Appl. No.: 568,278

[22] Filed: Jan. 4, 1984

Related U.S. Application Data

[63] Continuation of Ser. No. 318,265, Nov. 4, 1981.

[30] Foreign Application Priority Data

Nov. 12, 1980 [JP] Japan ................... 55-159245

[51] Int. Cl.³ ............................... A61B 1/00
[52] U.S. Cl. ........................ 128/4; 222/399; 239/351; 604/67
[58] Field of Search .......................... 128/4-8, 128/10, 11, 15, 16, 200.14; 433/30, 31; 222/61, 136, 399; 604/27, 31, 33, 39, 67, 139, 150; 239/332, 351, 413-415

[56] References Cited

U.S. PATENT DOCUMENTS 3,001,288  9/1961  Freedman ................... 433/31
3,986,266  10/1976 Vellender .................... 433/30
4,267,947  5/1981  Wassenstram ............... 222/399

FOREIGN PATENT DOCUMENTS 2426771  12/1974  Fed. Rep. of Germany ......... 128/6
2926921  2/1980   Fed. Rep. of Germany ......... 128/4

Primary Examiner—Edward M. Coven
Assistant Examiner—Max F. Hindenburg

[57] ABSTRACT

An endoscope apparatus comprises an endoscope body in which an air supply pipe and a water supply pipe are included, and an air supply unit connected to the endoscope body. The endoscope apparatus includes an air supply switch and a water supply switch arranged in an operating section, and a drive signal generator being adapted to receive output signals from these switches, an air supply pump connected to the air supply pipe, a water supply pump connected via a water vessel to the water supply pipe and having an output higher than the air supply pump. The air supply pump is driven responsive to the drive signal from the drive signal generator to achieve normal air supply for a time period during which the air supply switch is closed. The water supply pump is driven to perform water supply for a first predetermined time period starting from the instant when the water supply switch is closed, and the air supply pump is again driven to achieve water removing air supply for a second predetermined time period after the finish of the first predetermined time period.

1 Claim, 13 Drawing Figures

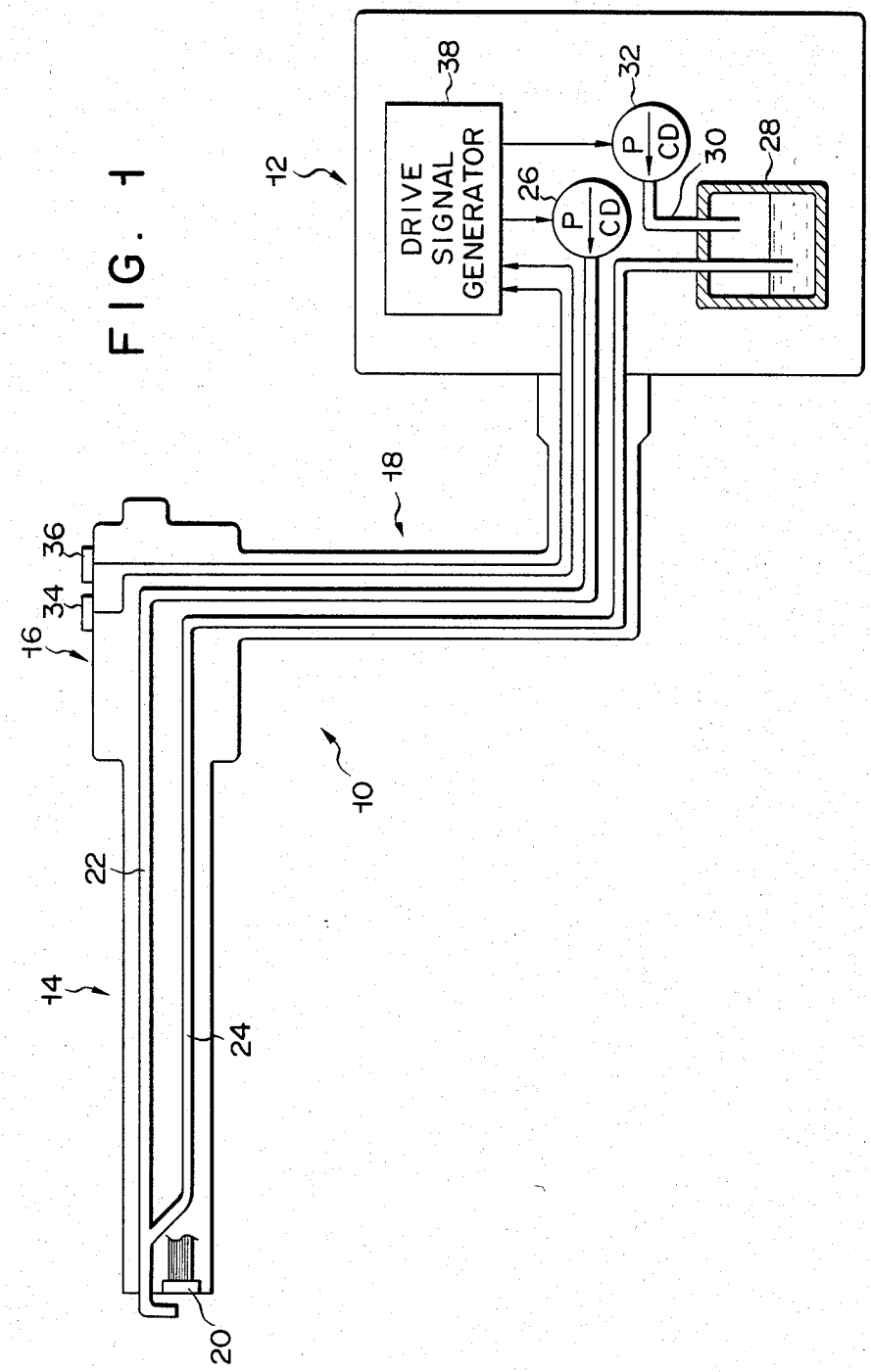

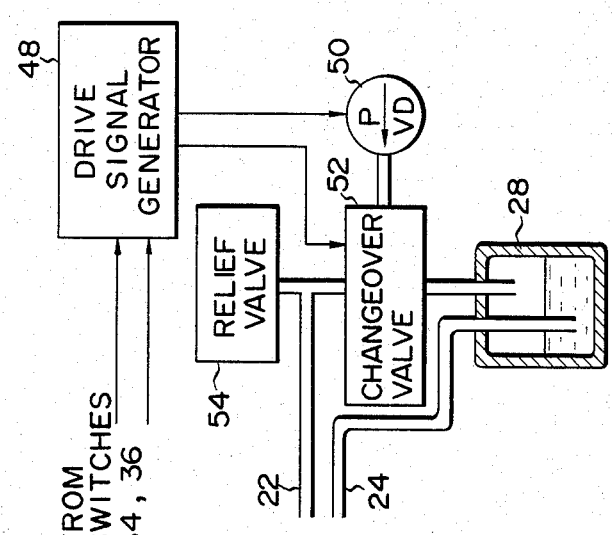
FIG. 4
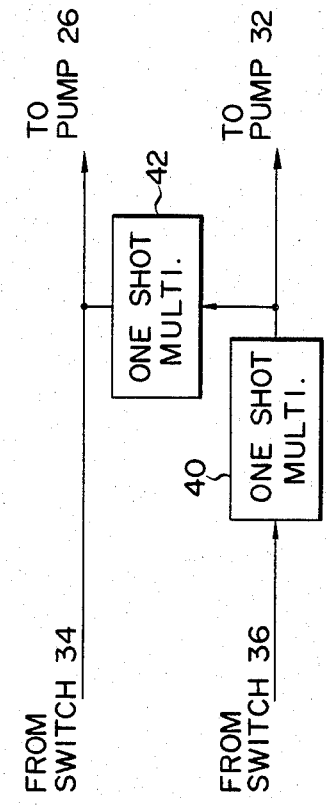
FIG. 2
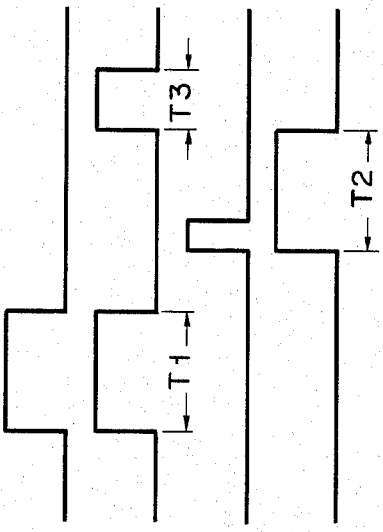
FIG. 3A
FIG. 3B
FIG. 3C
FIG. 3D

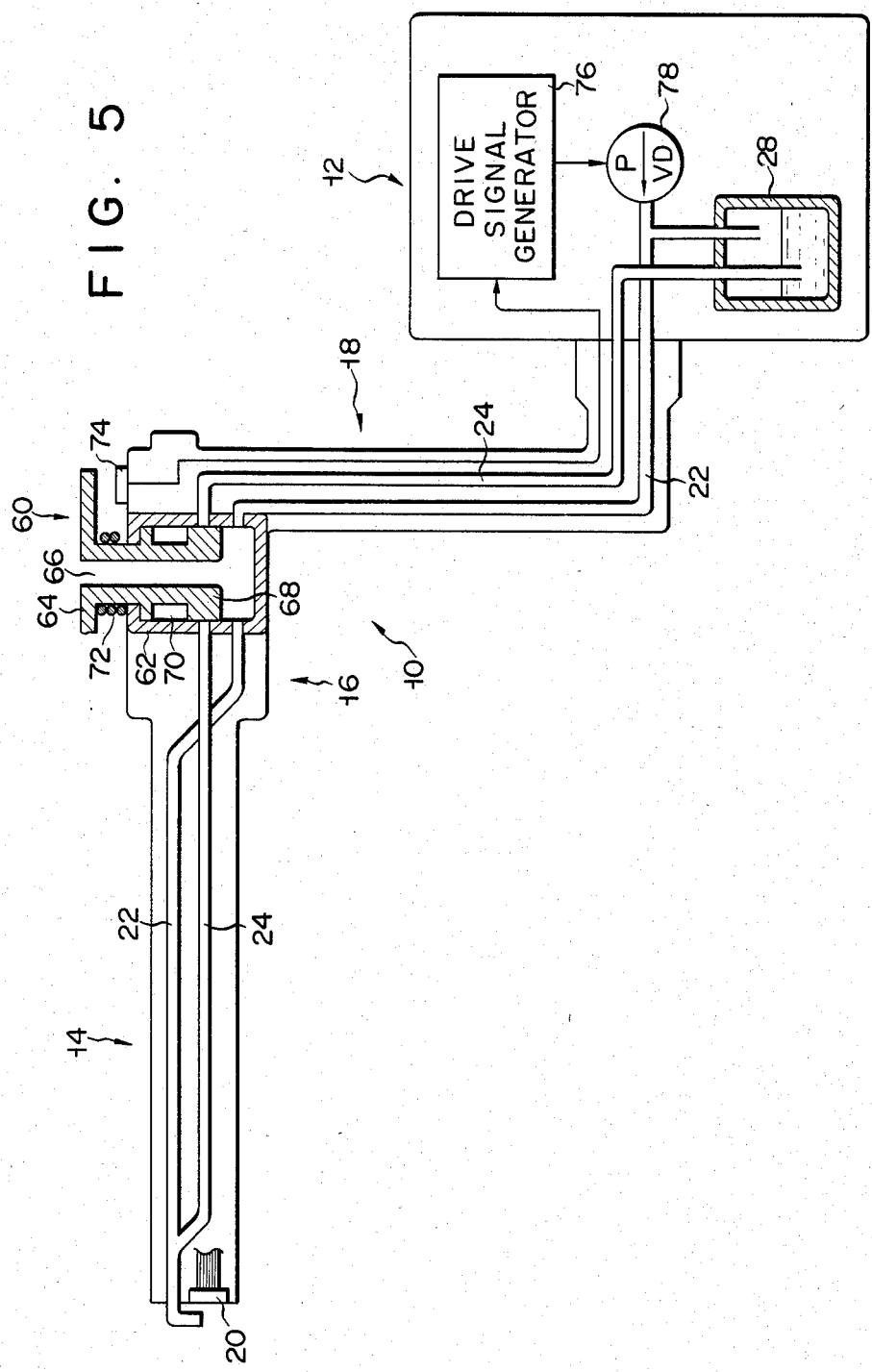

ENDOSCOPE APPARATUS

This application is a continuation of application Ser. No. 318,265, filed Nov. 4, 1981.

BACKGROUND OF THE INVENTION

The present invention relates to an endoscope apparatus and more particularly, to an air and water supply mechanism employed in the endoscope apparatus.

When the coeliac cavity of a human body is viewed using the endoscope, mucus and leftovers are often adhered to the surface of a viewing window of the endoscope to disturb the field of view. The conventional countermeasure of preventing the disturbance of viewing field was to attach to the foremost end of the endoscope a nozzle through which water was jetted to clean the viewing window and air was then jetted to the viewing window to remove water drops left on the surface of the viewing window. This air supply to remove water or water drops from the surface of viewing window (which will be hereafter referred to as water removing air supply) is more effective and the field of view through the viewing window can be restored more quickly when the force to supply air is large.

On the other hand, in addition to removing water or water drops from the surface of viewing window, water removing air supply also serves to inflate the coeliac cavity to some extent, thus taking the coeliac cavity ready and easy to be viewed. This air supply to inflate the coeliac cavity (which will be hereafter referred to as normal air supply) sometimes causes such danger that the coeliac cavity is ruptured when an air supply pressure is too high. It is therefore desirable to keep the air supply pressure low in normal air supply.

The conventional endoscope apparatus had a pump to supply air and water and the pump was driven at same output (or pressure) to supply air and water. This made it dangerous to set supply pressure high and supply pressure was kept low accordingly. The capability of cleaning the viewing window was therefore low and water or water drops were not completely removed from the surface of the viewing window either after cleaning. In other words, the field of view was neglected for the sake of safety.

SUMMARY OF THE INVENTION

The object of the present invention is to provide an endoscope apparatus capable of safely carrying out normal air supply and effectively achieving water removing air supply.

This object of the present invention can be attained by an endoscope apparatus comprising an endoscope body, air and water supply pipes arranged inside the endoscope body and one end of each of air and water supply pipes extending to the foremost end of the endoscope body, a water vessel connected to the other end of the water supply pipe, a pump connected to the other end of the air supply pipe and the water vessel, which being selectively driven to supply air to the air supply pipe or to supply water from the water vessel to the water supply pipe, a detector for generating a signal responsive to the start of water supply through the water supply pipe, and a drive signal generator for applying, responsive to the output signal of the detector, a drive signal to the pump to make the water supply pressure higher than the air supply pressure.

BRIEF DESCRIPTION OF THE DRAWINGS

FIG. 1 is a block diagram showing a first embodiment of an endoscope apparatus according to the present invention;

FIG. 2 is a circuit diagram showing a drive signal generator employed in the first embodiment;

FIGS. 3A through 3D are time charts showing the operation of an endoscope apparatus shown in FIG. 1;

FIGS. 4 through 6 are block diagrams showing second, third and fourth embodiments of an endoscope apparatus according to the present invention;

DETAILED DESCRIPTION OF THE PREFERRED EMBODIMENTS

Figure 7:
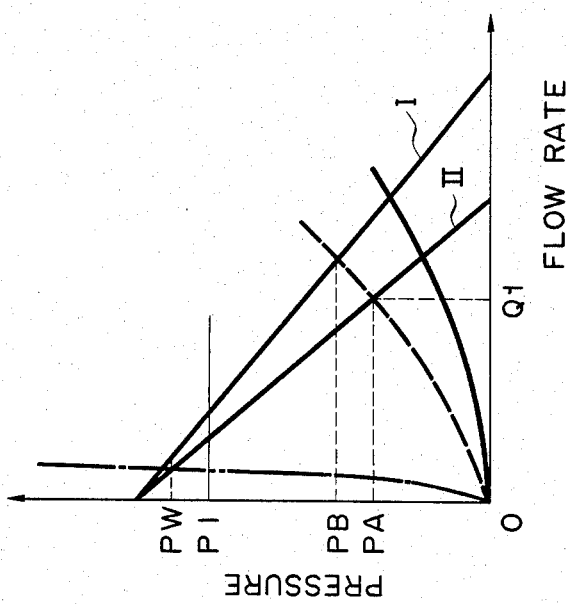
FIG. 7 is a graph showing the characteristic between the pressure and flow rate attained by the fourth embodiment.

An embodiment of an endoscope apparatus according to the present invention will be now described referring to the drawings. The endoscope apparatus shown in FIG. 1 is roughly consisted by an endoscope body 10 and an air supply unit 12. The endoscope body 10 comprises an insertion section 14 inserted into the coeliac cavity of human bodies, an operating section 16 for operating the movement of the insertion section 14, and a universal cord 18 connected to the air supply unit 12. A viewing window 20 having an objective is arranged at the foremost end of the insertion section 14 and one end of an image guide is faced to the viewing window 20. The endoscope body 10 includes an air supply pipe 22 and a water supply pipe 24. One ends of air and water supply pipes 22 and 24 are combined with each other at the foremost end of the insertion section 14 and the foremost end of the combined portion is passed through the foremost end of the insertion section 14 and opened facing the surface of the viewing window 20. The other ends of the air and water supply pipes 22 and 24 are connected through the universal cord 18 to the discharging opening of an air supply pump 26 arranged in the air supply unit 12 and to a water vessel 28 which serves as a water supply source, respectively. The other end of water supply pipe 24 is sunk and opened in water in the water supply vessel 28. One end of an air supply pipe 30 is opened in a space above water in the water vessel 28 while the other end thereof is connected to the discharging opening of a water supply pump 32. The air supply pump 26 generates relatively low pressure, e.g. 0.3 kg/cm² at maximum and the water supply pump 32 generates relatively high pressure, e.g. 1.0 kg/cm² at maximum. Air and water supply switches 34 and 36 are arranged at the operating section 16 and output signals are supplied from these switches 34 and 36 to a drive signal generator 38 arranged in the air supply unit 12. The drive signal generated from the drive signal generator 38 is supplied to the air and water supply pumps 26 and 32.

The drive signal generator 38 has such arrangement as shown in FIG. 2. The output signal of the air supply switch 34 is supplied to the air supply pump 26 and the output signal of the water supply switch 36 is supplied to an input terminal of a one-shot multi-vibrator 40. An output signal of the one-shot multi-vibrator 40 is supplied to the water supply pump 32 and to an input terminal of a one-shot multi-vibrator 42. An output signal of the one-shot multi-vibrator 42 is supplied to the air supply pump 26.

The operation of this embodiment will be now described. The air supply switch 34 is closed to carry out normal air supply after the insertion section 14 is inserted into the coeliac cavity. A signal of level H shown in FIG. 3A is generated to operate the air supply pump 26 as shown in FIG. 3B and normal air supply is thus carried out at low pressure of 0.3 kg/cm$^2$. Air is discharged through the air supply pipe 22 into the coeliac cavity to inflate it. Namely, normal air supply is continued during the time period of T1 when the air supply switch 34 is closed.

The operation of cleaning the viewing window 20 when the viewing window 20 is made dirty will be now described. The water supply switch 36 is closed in this case. The water supply switch 36 once closed may be opened when the output of this switch 36 becomes of level H as shown in FIG. 3C. Namely, the switch 36 may be adapted to output a pulse of level H. The one-shot multi-vibrator 40 continues to generate an output signal of level H only for a predetermined time period T2 (three seconds, for example) responsive to the rising of this pulse, and the water supply pump 32 is driven at output pressure of 1.0 kg/cm$^2$ for a first predetermined time period T2, as shown in FIG. 3D, starting from the time when the water supply switch 36 is closed. Water in the water vessel 28 is thus jetted through the water supply pipe 24 onto the viewing window 20 to thereby clean the viewing window 20. When time period T2 passes and the output signal of the one-shot multi-vibrator 40 becomes of level L, the operation of the water supply pump 32 is stopped. However, the falling of this signal is detected by the one-shot multi-vibrator 42, which supplies an output signal of level H only for a second predetermined time period T3 (two seconds, for example) to the air supply pump 26. The air supply pump 26 is thus driven only for predetermined time period T2, as shown in FIG. 3B, after the water supply pump 32 is deenergized. As the result, water removing air supply is carried out to blow away water or water drops from the surface of viewing window 20.

According to this embodiment, an endoscope apparatus is provided, which is capable of preventing damage to the coeliac cavity due to excess water supply and also capable of being easily operated since water supply is made only for the first predetermined time period and water removing air supply is automatically carried out only for the second predetermined time period after the finish of water supply.

Another embodiments of the present invention will be now described. Same parts as those of first embodiment are represented by same numerals and description of these parts will be omitted. FIG. 4 is a block diagram showing an air supply unit employed in the second embodiment. Output signals from air and water supply switches 34 and 36 are supplied to a drive signal generator 48, whose output signal is supplied to control terminals of an air supply pump 50 and a changeover valve 52, output of the air supply pump 50 being variable. The changeover valve 52 comprises a three-port two-position double solenoid electromagnetic valve, whose first port is connected to a discharging opening of the air supply pump 50, whose second port to a water vessel 28, and whose third port to a relief valve 54 and an air supply pipe 22. The end of the second port is opened in a space above water in the water vessel 28. The end of a water supply pipe 24 is sunk and opened in water in the water vessel 28.

The operation of the second embodiment is as follows. The air supply switch 34 is closed to achieve normal air supply. A signal of level H is generated and the drive signal generator 48 drives the air supply pump 50 to have output pressure of 0.3 kg/cm$^2$ only for a time period during which the signal of level H is being supplied to the drive signal generator 48, and generates signal to communicate the air supply line 22, i.e., to communicate the first port with the third port. As the result, the output air flow of the air supply pump 50 is transmitted to the air supply pipe 22 to achieve normal air supply. Namely, normal air supply is carried out only for the time period during which the air supply switch 34 is closed. When the water supply switch 36 is closed, a signal of level H is generated from the switch 36. The drive signal generator 48 detects the rising of the output signal from the water supply switch 36 and thereafter generates a drive signal only for predetermined time period T2 to thereby drive the air supply pump 50 to have output pressure of 1.0 kg/cm$^2$ and to communicate the changeover valve 52 with first and second ports. As the result, the output air of the air supply pump 50 is transmitted to the water vessel 28 and water in the water vessel 28 is jetted via the water supply pipe 24 onto the surface of the viewing window 20 to clean it. When predetermined time period T2 passes, the drive signal generator 48 produces a drive signal only for predetermined time period T3 to change output pressure of the air supply pump 50 to 0.3 kg/cm$^2$ and to communicate the changeover valve 52 with first and third ports. As the result, output pressure of air supply pump 50 of 0.3 kg/cm$^2$ is transmitted to the air supply pipe 22 to achieve water removing air supply. Namely, also in this embodiment, normal air supply is carried out only for the desired time period during which the air supply switch 34 is closed and cleaning water supply and subsequent water removing air supply are automatically performed only for the first and second predetermined time periods. Air supply pressure depends upon the pressure inside the coeliac cavity. When pressure in the coeliac cavity is low, pressure of the air supply unit 24 is made low to increase the amount of air supplied. When pressure in the coeliac cavity is high, pressure of the air supply unit 24 is made high to reduce the amount of air supplied. This embodiment uses the relief valve 54 to achieve such safety performance. When pressure in the coeliac cavity is higher than a predetermined value, the amount of air supplied is made zero. The pump 50 delivers pressure of 0.2 kg/cm$^2$ when the pressure in the coeliac cavity is 0. Relief pressure of the relief valve 54 is set at 0.23 kg/cm$^2$. This embodiment employs the variable delivery pump 50, thus enabling the air supply unit 24 to be small-sized and light-weighted.

FIG. 5 is a block diagram showing a third embodiment of the present invention. Air and water supply pipes 22 and 24 are cut in the operating section 16 and a changeover valve 60 is interposed therein. The valve 60 comprises a cylinder 62 and a piston 64 inserted therein. A leak hole 66 is formed in the center portion of the piston 64 and a larger-diameter portion 68 and a communicating recess 70 are formed on the outer circumference of the piston 64. The piston 64 is urged by a coil spring 72 in the outward direction of the operating section 16. The cut end face of each of the air and water supply pipes 22 and 24 is opened at the inner circumferential surface of the cylinder 62. When the piston 64 is left urged by the spring 72, the air supply pipe 22 is therefore communicated through a space formed between bottoms of the piston 64 and cylinder 62 and the water supply pipe 24 is blocked by the larger diameter portion 68 of the piston 64, as shown in FIG. 5. On the other hand, when the piston 64 is pushed down by the finger or the like of an operator against the urging force of the spring 72, the air supply pipe 22 is blocked by the larger diameter portion 68 of the piston 64 and the water supply pipe 24 is communicated through the communicating recess 70. A switch 74 is arranged at a position where it can be operated by an upper projection of the piston 64 when the piston 64 is pushed down. An output signal of the switch 74 is supplied to a drive signal generator 76 in an air supply unit 12, whose output signal is supplied to a variable delivery air supply pump 78. A discharging opening of the air supply pump 78 is connected to the air supply pipe 22 and a part of air supply pipe 22 is inserted into a water vessel 28. The others are same in arrangement as those in already-described embodiments.

The operation of this embodiment shown in FIG. 5 is as follows. When a power source which is not shown is turned on, the air supply pump 78 is driven at output pressure of 0.3 kg/cm² responsive to a drive signal from the drive signal generator 76. Since the piston 64 which serves as the changeover valve 60 is urged by the spring 72 in the outward direction of the operating section 16 as shown in FIG. 5, the water supply pipe 24 is blocked and the air supply pipe 22 is communicated. However, air supplied through the air supply pipe 22 into the cylinder 62 escapes outside through the leak hole 66 and is not therefore fed into the air supply pipe 22 arranged inside the insertion section 14, thus leaving air supply into the coeliac cavity not achieved. Normal air supply is achieved by closing the leak hole 66 by the finger or the like of an operator. When the leak hole 66 is closed by the finger, air in the cylinder 62 is discharged into the coeliac cavity through the air supply pipe 22 arranged inside the insertion section 14. Namely, normal air supply is carried out at low pressure of 0.3 kg/cm² only for the time period during which the leak hole 66 is closed, and when a desired amount of air is supplied, the leak hole 66 is opened to finish normal air supply.

For the purpose of supplying water to clean the viewing window 20, the piston 64 is pushed down closing the leak hole 66 by the finger. When the piston 64 is pushed down, the air supply pipe 22 is blocked by the larger diameter portion 68 of the piston 64 while the water supply pipe 24 is communicated through the communicating recess 70. In addition, the switch 74 is closed by the projection of the piston 64 and a signal of level H is supplied from the switch 74 to the drive signal generator 76 whereby a drive signal is generated and the air supply pump 78 is driven at output pressure of 1.0 kg/cm². Water supply is therefore achieved at high pressure. The piston 64 must be left pushed down closing the leak hole 66. As apparent from the above, the third embodiment enables water supply to be performed only for the time period during which the piston 64 is pushed down.

When a desired amount of water is supplied, the finger is removed from the piston 64. The piston 64 is returned by the spring 72 to its original position shown in FIG. 5 and the water supply pipe 24 is again blocked while the air supply pipe 22 is communicated. The switch 74 is opened and an output signal of the switch 74 becomes of level L. Even if the output signal of the switch 74 is lowered in level, the drive signal generator 76 keeps output pressure of the air supply pump 78 1.0 kg/cm² for a short time period (two seconds, for example) after the output signal of the switch 74 falls, and then changes it to 0.3 kg/cm². Therefore, water removing air supply can be achieved at high output pressure when the leak hole 66 is closed by the finger only for the short time period after the piston 64 is returned by the spring 72 to its original position.

According to the third embodiment as described above, normal air and water supplies can be achieved only for the desired time periods and water removing air supply can be automatically performed only for the predetermined time period after water supply. In addition, water supply and water removing air supply can be performed at higher output than normal air supply, thus allowing higher effect to be attained. Instead of using the variable delivery pump 78, another pump having an different output may be arranged and turned on and off to control the third embodiment.

Figure 6:
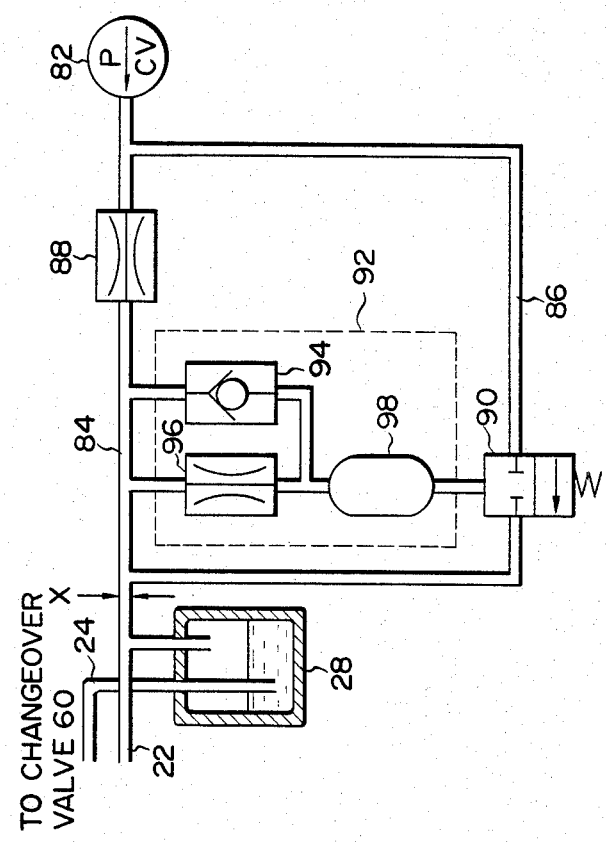

FIG. 6 is a block diagram showing an air supply unit employed in a fourth embodiment of the present invention. The other portion i.e. endoscope body of this fourth embodiment is same as that of the third embodiment shown in FIG. 5. A discharging pipe of an air supply pump 82 is divided to a main pipe 84 and a bypass pipe 86, which are combined with each other respectively through a needle valve 88 and an on-off valve 90 and connected to a changeover valve 60 arranged in the operating section 14. The on-off valve 90 is a changeover valve of two-port two-position pilot type. To the output of the needle valve 88 of the main pipe 84 is connected an off-delay circuit 92, which comprises a check valve 94, needle valve 96 and tank 98, and whose output is supplied to the control terminal of the on-off valve 90. A part of an air supply pipe 24 is connected to a water vessel 28 and water in the water vessel 28 is supplied through a water supply pipe 24 to the changeover valve 60.

Under the initial state when the power source is turned on, the air supply pump 82 operates in such a way that the characteristic between pressure and flow rate is represented as shown by a line I in FIG. 7. The piston 64 of the changeover valve 60 is urged by the spring 72 in the outward direction of the operation section 16 under the initial state, similarly to that in the third embodiment. Air discharged from the air supply pump 82 therefore passes through the main pipe 84, is reduced in pressure by the needle valve 88, and then fed into the space formed between bottoms of the piston 64 and cylinder 62. Similarly to the third embodiment, however, air thus fed into the space is discharged outside through the leak hole 66 and no air supply is performed. Water supply is not carried out either, since the water supply pipe 24 is blocked.

Providing that pressure in the coeliac cavity is zero at this time, the relation between pressure and flow rate at a point X in FIG. 6 is as shown by a solid curve in FIG. 7. Namely, since the leak hole 66 is left opened, the resistance of the pipe path is low and pressure is left unchanged even when flow rate is increased. Curves represented by broken and one-dot and -dash lines in FIG. 7 show relations between pressure and flow rate at the point X in FIG. 6 at the time of air and water supplies. A solid line extending transversely in FIG. 7 represents pilot pressure PI of the off-delay circuit 92. As apparent from the above, pressure at the point X in FIG. 6 is lower than the pilot pressure PI under the initial state and at the time of air supply. The on-off valve 90 is thus kept off and the by-pass pipe 86 is left blocked. Therefore, output pressure of the pump 82 is reduced by the needle valve 88 and then transmitted to the point X, so that the characteristic of pump 82 at the point X is represented by a line II which shows that both pressure and flow rate are lower than those represented by line I.

When the leak hole 66 of the piston 64 is closed thereafter, normal air supply is carried out. Since the resistance value of whole pipe path is increased due to the resistance of the air supply pipe 22, the characteristic at the point X draws a curve shown by the broken line in FIG. 7. Pressure and flow rate at the point X are PA and Q1, respectively. Since the pressure PA is smaller than the pilot pressure PI, the by-pass pipe 86 is still left blocked.

When the piston 64 is pushed down with the leak hole 66 closed, water supply is performed as seen in the third embodiment. Since the liquid resistance of the pipe path relative to water is remarkably larger than that relative to air, the characteristic at the point X draws a curve shown by the one-dot and -dash line in FIG. 7. Pressure PW is larger than the pilot pressure PI at this time, and the on-off valve 90 is therefore turned on and the by-pass pipe 86 is communicated.

When the piston 64 is then returned to its original position with the leak hole 66 closed, water supply is stopped while air supply is started. Pressure at the point X becomes air supply pressure PA lower than the pilot pressure PI in case of no off-delay circuit 92, but the on-off valve 90 is thereafter kept on by the off-delay circuit 92 for a predetermined time period. Therefore, the main pipe 84 is communicated with the by-pass pipe 86 for this predetermined time period. In addition, these main and by-pass pipes 84 and 86 are arranged in parallel. Therefore, the resistance of whole pipe path in the air supply unit becomes lower and the characteristic of pump 82 draws line I in FIG. 7. At the time when the off-delay circuit 92 is operated, air supply pressure PB thus becomes larger than pressure PA at the time of normal air supply. Water removing air supply is therefore achieved effectively after water supply. After the finish of operation of off-delay circuit 92, the on-off valve 90 becomes off, subsequent pump characteristic draws line II in FIG. 7, amount of air supplied is reduced, and normal air supply is again started. When the leak hole 66 is opened thereafter, air supply is finished.

According to the fourth embodiment, air supply amount and pressure of the pump are increased upon water removing air supply, so that water drops left after cleaning on the viewing window are evaporated for an extremely short time period. Instead of arranging the by-pass pipe 86 to the output of one air supply pump 82 to adjust liquid resistance, another pump may be arranged to the input of on-off valve 90 to change air supply pressure. The fourth embodiment needs only the changeover valve 60 in the operating section 16, making it unnecessary to use the switch 74 shown in FIG. 5. Therefore, this fourth embodiment can be applied to the conventional endoscope body without any change added.

Figure 8:
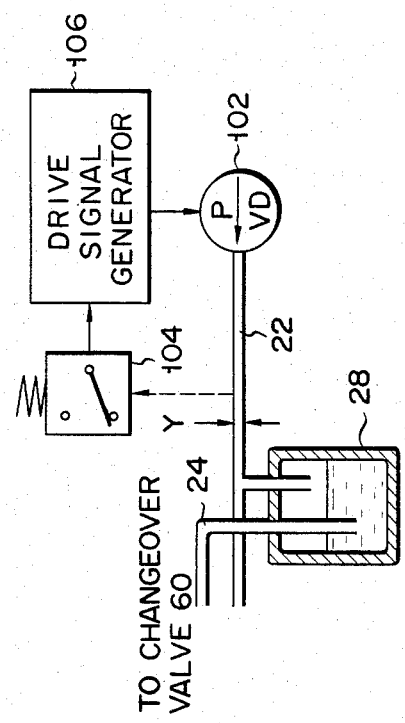
FIG. 8 is a block diagram showing a fifth embodiment of an endoscope apparatus according to the present invention.

FIG. 8 is a block diagram showing an air supply unit employed in a fifth embodiment of the present invention. The endoscope body of the fifth embodiment is same as that of the third embodiment shown in FIG. 5. A discharging opening of a variable delivery air supply pump 102 is connected to an air supply pipe 22. A pressure switch 104 operating responsive to pressure in the pipe 22 is arranged on the way of the air supply pipe 22 and an output signal of the pressure switch 104 is supplied to a drive signal generator 106, whose output signal is supplied to the air supply pump 102. When pressure in the air supply pipe 22 becomes larger than a predetermined value PY, the pressure switch 104 is turned on to generate a signal of level H.

Figure 9:
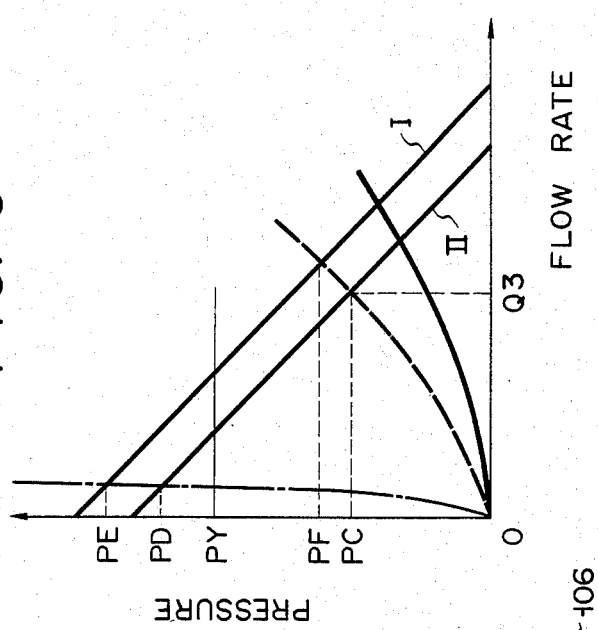
FIG. 9 is a graph showing the operating characteristic of the endoscope apparatus shown in FIG. 8.

Under the initial state when the power source is turned on, the air supply pump 102 is operated according to the characteristic represented by a line II in FIG. 9. Air supplied from the air pump 102 to the changeover valve 60 is discharged outside through the leak hole 66. Solid, broken and one-dot and -dash lines in FIG. 9 show relations between pressure and flow rate at a point Y in FIG. 8 at the time of initial state, air supply and water supply.

When the leak hole 66 is closed, normal air supply is performed at air supply amount of Q3. Since pressure in the pipe path 22 is PC at this time, the pressure switch 104 is not turned on yet. When the piston 64 is then pushed down with the leak hole 66 closed to supply water, water supply pressure becomes PD. Since PD is larger than PY, the pressure switch 104 is turned on and the drive signal generator 106 causes the air supply pump 102 to operate according to the characteristic represented by a line I in FIG. 9. Therefore, water supply is carried out at water supply pressure of PE higher than PD and the cleansing of viewing window 20 is progressed. On the other hand, when the piston 64 is returned to its initial position with the leak hole 66 closed, water supply is finished while air supply is started. Pressure of air supply pipe 22 is thus reduced lower than PY, the pressure switch 104 is turned off, and the output signal of the pressure switch 104 becomes of level L. However, the drive signal generator 106 thereafter keeps the driving state of the air supply pump 102 unchanged for a predetermined time period (three seconds, for example), detecting the fall of the output signal of the pressure switch 104. Since the air supply pump 102 is thus operated according to the characteristic represented by line I in FIG. 9, air supply pressure PF at this time of water removing air supply is higher than PC at the time of normal air supply. As the result, air is powerfully jetted onto the viewing window 20 to quickly remove water or water drops from the viewing window 20. When the predetermined time period passes, the output characteristic of pump 102 draws line II in FIG. 9.

According to the fifth embodiment, the output of the pump becomes large at the time of water supply and water removing air supply, to thereby allow the viewing window to be cleaned completely.

Figure 10:
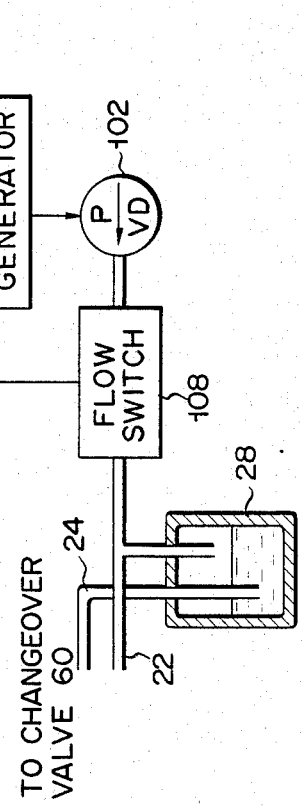
FIG. 10 is a block diagram showing a sixth embodiment of an endoscope apparatus according to the present invention.

FIG. 10 is a block diagram showing an air supply unit employed in a sixth embodiment of the present invention, which is different from the fifth embodiment in that a flow switch 108 is arranged instead of the pressure switch 104. The flow switch 108 is a flow meter of contact type, and when flow rate in the pipe path 22 becomes lower than a predetermined value, the flow switch 108 is turned on to generate a signal of level H.

The operation of the sixth embodiment is same as that of the fifth embodiment and descritioin of the former's operation will be therefore omitted. The sixth embodiment is intended to detect the change of flow rate instead of change of pressure to thereby change an output delivery of the pump 102. Flow rate can be more accurately detected than pressure.

According to the present invention as described above, normal air supply is performed at low pressure but water supply and water removing air supply are carried out at high pressure, so that an endoscope apparatus of high safety and having an always-cleaned viewing window can be provided. It should be understood that the present invention is not limited to the embodiments as described above and can be variously changed without departing from the scope of the invention.

What is claimed is:

1. An endoscope apparatus comprising:

an endoscope body including an endoscope insertion section having a foremost end and a viewing window arranged at said foremost end;

an air supply pipe and a water supply pipe disposed within said endoscope body and integrally connected with each other at one end to form a discharge conduit through which a source of air and water is alternately directed in front of said viewing window, said air and water supply pipes being respectively divided into two sections;

a water supply source connected to said water supply pipe and an air supply source connected to said air supply pipe;

a variable output pump means connected to the upstream sides of said air supply source and to said water supply source and having first and second modes of output, the second output being higher than the first output;

a change-over valve arranged alternately to connect said sections of air and water supply pipes to said foremost end and formed by a cylinder having an inner circumferential face connected with said sources of air and water supply, and a piston within said cylinder for selectively and alternatively supplying air to said air supply pipe and water to said water supply pipe, the piston having a first diameter portion and second diameter portion which is larger than the first diameter portion and a leak hole connecting the inside of the cylinder with the outside of the cylinder, the piston being normally urged outwardly by a spring to shut off said water supply source by means of said second diameter portion and to connect said air supply source through said first diameter portion, and when pushed down into said cylinder against said spring, to shut off the air supply by means of said second diameter portion and thereby connect said water supply through said first diameter portion;

a detector switch arranged adjacent to said change-over valve and generating a detection signal when said piston is pushed down into said cylinder; and a drive signal generator for supplying a first signal to said variable output pump means causing said pump means to be operated in the second mode, and after a predetermined period of time after the detection signal is generated, for supplying a second signal to said pump means thereby causing said pump means to be operated in the first mode.

* * * * *